(12) United States Patent
Daigneault et al.

(10) Patent No.: US 7,365,203 B2
(45) Date of Patent: Apr. 29, 2008

(54) PROCESS FOR THE SYNTHESIS OF 6-AMINO-4-(3-CHLORO-4-FLUORO-PHENYLAMINO)-7-ETHOXY-QUINOLINE-3-CARBONITRILE

(75) Inventors: Sylvain Daigneault, Laval-sur-le-Lac (CA); Ronald Stanley Michalak, Congers, NY (US); Michel Bernatchez, Montreal (CA)

(73) Assignee: Wyeth, Madison, NJ (US)

( * ) Notice: Subject to any disclaimer, the term of this patent is extended or adjusted under 35 U.S.C. 154(b) by 533 days.

(21) Appl. No.: 10/939,008

(22) Filed: Sep. 10, 2004

(65) Prior Publication Data

US 2005/0065181 A1 Mar. 24, 2005

Related U.S. Application Data

(60) Provisional application No. 60/503,106, filed on Sep. 15, 2003.

(51) Int. Cl.
*C07D 215/38* (2006.01)

(52) U.S. Cl. .................................................. 546/160
(58) Field of Classification Search ................. 546/160
See application file for complete search history.

(56) References Cited

U.S. PATENT DOCUMENTS

| 6,002,008 | A | 12/1999 | Wissner et al. | |
| 6,384,051 | B1 * | 5/2002 | Frost et al. | 514/313 |
| 6,821,988 | B2 * | 11/2004 | Wissner et al. | 514/313 |

OTHER PUBLICATIONS

Wissner, J Med Chem, vol. 46, pp. 49-63, published on the web, Dec. 2, 2002.*
Wissner, A.; et al.; Bioorganic & Medicinal Chemistry Letters 12:2893-2897 (2002).
Wissner, A.; et al.; J. Med. Chem. 46:49-63 (2003).

* cited by examiner

*Primary Examiner*—D. Margaret Seaman
(74) *Attorney, Agent, or Firm*—Stephen E. Johnson

(57) ABSTRACT

The present invention provides a process for the preparation of 6-amino-4-(3-chloro-4-fluoro-phenylamino)-7-ethoxy-quinoline-3-carbonitrile comprising the steps and products disclosed within this application.

1 Claim, No Drawings

PROCESS FOR THE SYNTHESIS OF 6-AMINO-4-(3-CHLORO-4-FLUORO-PHENYLAMINO)-7-ETHOXY-QUINOLINE-3-CARBONITRILE

This application claims priority from provisional application Ser. No. 60/503,106, filed Sep. 15, 2003, the entire disclosure of which is hereby incorporated by reference.

BACKGROUND OF THE INVENTION

The two most frequently used synthetic methods for the preparation of 3-cyano-4-quinolones or 3-carboalkyloxyquinolones are intramolecular Friedel-Crafts reactions and electrocyclic ring closures of N-(2-carboxyvinyl)-aniline derivatives. Friedel-Crafts conditions work well for electron rich anilines, moderately for unsubstituted anilines, and poorly or not at all for electron-deficient anilines and are not useful for large scale preparation of 3-cyano-4-quinolones especially utilizing electron deficient anilines. The electron withdrawing groups of the aniline reduce the nucleophilicity of the aromatic ring to the point that side reactions compete with, if not dominate, the desired intramolecular condensation.

Thermal conditions for electrocyclic ring closures of N-(2-carboxyvinyl)-aniline derivatives typically require temperatures in excess of 240° C. In U.S. Pat. No. 6,002,008 the construction of 3-cyano-4-quinolones has been achieved by electrocyclic ring closure reactions of N-(2-carboxyvinyl)aniline derivatives by heating to 260° C. in diphenyl ether. Thermal decomposition of either the final product and/or the starting material may compromise the purity of the final product as a result of the high temperature reaction conditions. As a result, reactions are often run at high dilution resulting in an inefficient large-scale process due to low throughput.

The production of 3-cyano-4-quinolones by electrocyclic ring closure suffers from all of the problems mentioned above. For example, it is known that 7-ethoxy-4-hydroxy-6-nitroquinoline-3-carbonitrile decomposes at 240° C. while the minimum temperature required for cyclization is 256° C.

There is a need for a process which overcomes the problem of thermal decomposition of intermediate compounds, including 6-amino-4-(3-chloro-4-fluoro-phenylamino)-7-ethoxy-quinoline-3-carbonitrile used to epidermal growth factor receptor (EGFR) inhibitors useful in the treatment of cancer.

The following experimental details are set forth to aid in an understanding of the invention, and are not intended, and should not be construed to limit in any way the invention set forth in the claims that follow thereafter.

BRIEF SUMMARY OF THE INVENTION

This invention relates to producing 6-amino-4-(3-chloro-4-fluorophenylamino)-7-ethoxy-quinoline-3-carbonitrile which comprises:
  (a) acylating 2-Amino-5-nitrophenol with an acylating agent to obtain 2-Acetamido-5-nitrophenol;
  (b) alkylating 2-Acetamido-5-nitrophenol of step (a) with an alkylating agent in the presence of a base to obtain 4-Acetamide-3-ethoxynitrobenzene
  (c) reacting 4-Acetamide-3-ethoxynitrobenzene of step (b) to obtain 4-Acetamido-3-ethoxy-aniline;
  (d) condensing 4-Acetamido-3-ethoxy-aniline of step (c) with (ethoxymethylene)cyanoacetate to yield 3-(4-acetamido-3-ethoxyaniline)-2-cyano-propenoic acid ethyl ester;
  (e) cyclizing 3-(4-Acetamido-3-ethoxyaniline)-2-cyano-propenoic acid ethyl ester of step (d) to yield 3-Cyano-7-ethoxy-4-hydroxy-6-acetylquinoline;
  (f) reacting 3-Cyano-7-ethoxy-4-hydroxy-6-N-acetylquinoine of step (e) with a chlorine-substituting reagent to obtain 4-Chloro-3-cyano-7-ethoxy-6-N-acetylquinoline, and then condensing with 3-chloro-4-fluoroaniline optionally in the presence of acid to yield N-[4-(3-chloro-4-fluoro-phenylamino)-3-cyano-7-ethoxy-guinolin-6-yl]-acetamide;
  (g) hydrolyzing N-[4-(3-chloro-4-fluoro-phenylamino)-3-cyano-7-ethoxy-quinolin-6-yl]-acetamide of step (f) with acid to yield 6-amino-4-(3-chloro-4-fluoro-phenylamino)-7-ethoxyquinoline-3-carbonitrile;
  (h) optionally converting 6-amino-4-(3-chloro-4-fluoro-phenylamino)-7-ethoxy-quinoline-3-carbonitrile to a pharmaceutically acceptable salt form thereof.

Pharmaceutical acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms ordialkylammonium salts containing 1-6 carbon atoms in each alkyl group, and trialkylammonium salts containing 1-6 carbon atoms in each alkyl group, when a compound of this invention contains an acidic moiety.

In accordance with this invention there is provided the following compounds and a process for the synthesis of 2-Acetamido-5-nitrophenol; 4-Acetamido-3-ethoxynitrobenzene, 3-(4-Acetamido-3-ethoxyaniline)-2-cyanopropenoic acid ethyl ester, 4-acetamido-3-ethoxy-aniline, 3-Cyano-7-ethoxy-4-hydroxy-6-N-acetylquinoline, 4-Chloro-3-cyano-7-ethoxy-6-N-acetylquinoline, and 6-amino-4-(3-chloro-4-fluoro-phenylamino)-7-ethoxy-quinoline-3-carbonitrile.

DETAILED DESCRIPTION OF THE INVENTION

The process of the invention is shown in Scheme I:

Scheme I

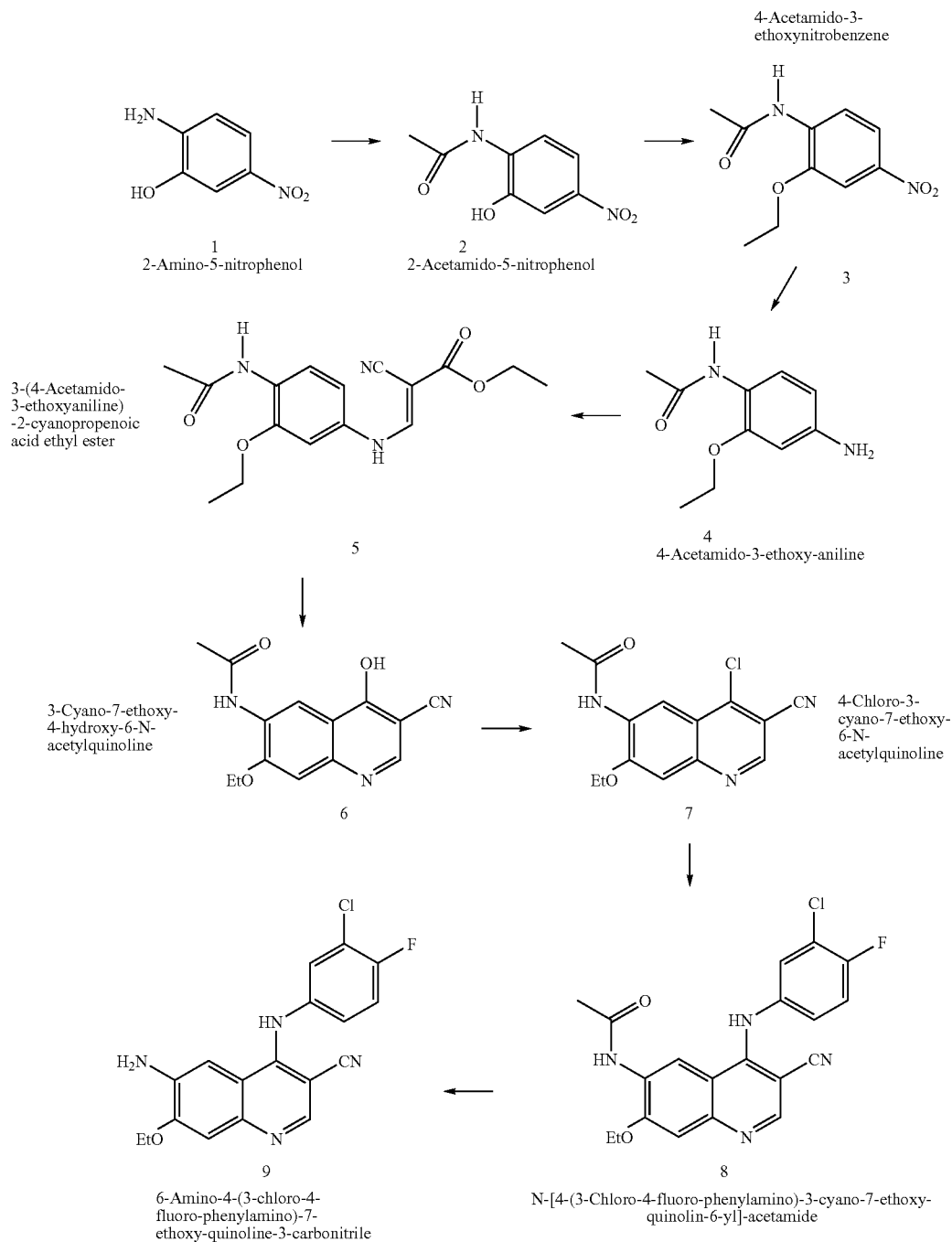

The acetylation of 2-Amino-5-nitrophenol 1 is performed by adding an acylating agent at 60° C. to a stirred suspension of 2-Amino-5-nitrophenol and acetic acid to yield 2-Acetamide-5-nitrophenol 2.

The alkylation of 2-Acetamido-5-nitrophenol 2 is performed by adding an alkylating reagent to yield 4-Acetamido-3-ethoxynitrobenzene 3.

4-Acetamido-3-ethoxynitrobenzene 3 in tetrahydrofuran (10 parts) was reduced to 4-Acetamido-3-ethoxy-aniline 4 under hydrogenation conditions (10% Pd/C wet, 50 psi, 2 hours). The concentrate was condensed by dilution with toluene and reaction with commercially available ethyl (ethoxymethylene)cyanoacetate at reflux for 16 hours. After the reaction reached completion, the mixture was cooled. The precipitated product was collected by filtration, washed and dried to yield 3-(4-Acetamido-3-ethoxyaniline)-2-cyanopropenoic acid alkyl ester 5.

3-(4-Acetamido-3-ethoxyaniline)-2-cyanopropenoic acid ethyl ester 5 was cyclized in a solvent at a temperature of about 230-258° C. (in a preferred embodiment the temperature was 250° C.) to yield 3-Cyano-7-ethoxy-4-hydroxy-6-N-acetylquinoline 6.

3-Cyano-7-ethoxy-4-hydroxy-6-N-acetylquinoline 6 was reacted with a chlorine-substituting reagent to yield 4-Chloro-3-cyano-7-ethoxy-6-N-acetylquinoline 7 followed by condensation with 3-chloro-4-fluoroaniline optionally in the presence of acid to yield N-[4-(3-Chloro-4-fluoro-phenylamino)-3-cyano-7-ethoxy-quinolin-6-yl]-acetamide 8.

N-[4-(3-Chloro-4-fluoro-phenylamino)-3-cyano-7-ethoxy-quinolin-6-yl]-acetamide 8 was hydrolyzed with acid to yield 6-amino-4-(3-chloro-4-fluoro-phenylamino)-7-ethoxy-quinoline-3-carbonitrile 9.

EXAMPLE 1

2-acetamido-5-nitrophenol

Acetic anhydride (398 g, 3.90 mol) was added to a stirred suspension of 2-amino-5-nitro-phenol (400 g, 2.60 mol) and acetic acid (1.60 L) at 62.5° C. The reaction mixture was stirred at 62.5° C. for 1 hour, and then cooled to room temperature. Water (2.00 L) was added over 20 minutes to the stirred reaction mixture. After stirring for 1 hour, the solid was collected by vacuum filtration and washed with water and heptane. Drying the product in vacuo at 60° C. yielded 486.7 g (96%, 99.5% by HPLC) of N-(2-hydroxy-4-nitro-phenyl)-acetamide. $^1$H NMR (DMSO-$d_6$) δ (ppm) 2.18 (s, 3H), 7.70 (m, 2H), 8.30 (d, 1H), 9.45 (s, 1H), 11.00 (s, 1H).

EXAMPLE 2

2-Acetamido-5-nitrophenol

A 5-L multi-necked flask equipped with a mechanical stirrer, reflux condenser, nitrogen inlet, 500-mL addition funnel, heating mantle, and a thermocouple attached to a temperature controller was charged with 400 g 2-Amino-5-nitrophenol. The flask was than charged with 1.6 L of acetic acid. The resulting mixture was stirred and warmed to 60±2° C. to achieve a suspension. While maintaining the temperature at 62.5±2.5° C. 398 g of acetic anhydride was added over 1.5 hours and stirred for one hour to 2-Acetamido-5-nitrophenol with less than 1% of 2-Amino-5-nitrophenol present. If necessary 37 mL of acetic acid was added to reduce the concentration of 2-Amino-5-nitrophenol. The reaction mixture was cooled to 20±5° C. and 2.00 L of water was added over 20 minutes and the suspension was stirred for one hour. Using vacuum filtration the suspension containing 2-Acetamido-5-nitrophenol was collected washed with water followed by a heptane wash, and dried in a vacuum. Yield 486.7 g (96%), strength 101.2%, mp>250° C., $^1$HNMR (DMSO $d_6$) δ1.42 (t, 3H), 2.20 (s, 3H), 4.25 (q, 2H), 7.78 (d, 1H), 7.78 (dd, 1H), 8.36 (d, 1H), 9.42 (s, 1H).

EXAMPLE 3

4-Acetamido-3-ethoxynitrobenzene

A 12-L, 4-necked flask equipped with a reflux condenser, nitrogen inlet, thermocouple, addition funnel, and mechanical stirrer was charged with 400 g 2-Acetamido-5-nitrophenol. The flask was charged with 790 g potassium carbonate and 2.0 L of dimethylformamide (DMF). The mixture was stirred and warmed to 60±2.50° C. 294 g of ethyl bromide or ethyl iodide was added over 10 minutes to one hour while maintaining a 60° C. internal temperature. The reaction mixture was stirred for at least one hour or until the mixture turned yellow and the concentration of 2-Acetamido-5-nitrophenol was less than 1%, if needed additional ethyl bromide or ethyl iodide was added to reduce the concentration of 2-Acetamido-5-nitrophenol present. The mixture was cooled to 20±5° C. 4 L of water was added and while maintaining a 25±5° C. internal temperature. The suspension was stirred for a minimum of 30 minutes and collected by vacuum filtration. The product was washed and the pH monitored for a pH of <8. If the pH was >8, the product was washed with 1.0 L portions of warm water until the pH was <8. The resultant product was washed with heptane and vacuum dried. Yield 98%, strength 98.6%, mp 164-165° C.

EXAMPLE 4

3-(4-Acetamido-3-ethoxyaniline)-2-cyano-propenoic acid ethyl ester

A 2-gallon Parr #2 hydrogenator was purged with nitrogen and charged with 10% palladium on carbon (35 g, 50% wet) and 4-Acetamido-3-ethoxynitrobenzene (420 g, 1.87 mol). The closed reactor was purged an additional 3 times with nitrogen and tetrahydrofuran (THF, 4.2 L) was added from a pressure bomb. The reactor was purged an additional 3 times with nitrogen and 3 times with hydrogen and the reaction mixture was hydrogenated at 50 psi at 28-30° C. for 3 hours using an uptake meter. After completion the reaction mixture was filtered and rinsed with THF (300 mL). A 6 L multi-neck flask with a mechanical stirrer, thermometer, still head for reduced pressure distillation, condenser, and receiver was charged with the filtrate using a THF rinse. The solution was concentrated to 840 mL. The filtrate was stirred with toluene (5.5 L) and ethyl(ethoxymethylene)cyanoacetate (475 g, 2.81 mol) and heated to reflux of 90° C. with stirring for 16 hours. The product was filtered and washed with toluene and dried with a vacuum to yield 3-(4-Acetamido-3-ethoxyaniline)-2-cyanopropenoic ethyl ester as a mixture of cis-trans isomers. Yield 534.0 g, 90.3%, $^1$H NMR (DMSO- $d_6$) δ1.25 (m, 6H), 1.38 (t, 6H), 2.10 (s, 3H), 3.35 (s, 3H), 4.05-4.30 (m, 8H), 6.95 (t, 2H), 7.10 (s, 1H), 7.25 (s, 1H), 7.85 (d, 2H), 8.30 (d, 2H), 8.50 (d, 2H), 9.00 (s, 2H), 10.70 (d, 2H).

EXAMPLE 5

3-Cyano-7-ethoxy-4-hydroxy-6-N-acetylquinoline

A 22 L 4-necked flask equipped with a reflux condenser, nitrogen inlet, two thermocouples attached to two independent temperature controllers, and a mechanical stirrer was charged with 210 g of 3-(4-Acetamido-3-ethoxyaniline)-2-cyanopropenoic acid ethyl ester. The flask was charged with 12.0 L of Dowtherm A. A nitrogen flow was introduced over the reaction, venting through the condenser. The mixture was stirred and warmed to 250±5° C. while maintaining the temperature and monitoring the reaction by high performance liquid chromatography (HPLC) to obtain >49% (relative area) 3-Cyano-7-ethoxy-4-hydroxy-6-N-acetylquinoline. The reaction mixture was cooled to room temperature. The solid was collected by filtration and washed with toluene. In a 2-L 4-necked flask, equipped with a water-cooled condenser, overhead stirring apparatus and $N_2$ blanket the solid and THF were combined. The mixture was stirred and warmed to reflux and maintained for a minimum of 30 minutes. The resultant mixture was cooled to room temperature, collected by filtration, washed with THF and vacuum dried to yield 3-Cyano-7-ethoxy-4-hydroxy-6-N-acetylquinoline. Yield 42%, strength 95.2%, mp>250° C., $^1$H NMR (DMSO-$d_6$) δ1.42 (t, 3H), 2.15 (s, 3H), 4.21 (q, 2H), 7.08 (s, 1H), 8.60 (s, 1H), 9.17 (s, 1H), 12.50 (s, 1H)

EXAMPLE 6

4-Chloro-3-cyano-7-ethoxy-6-N-acetylquinoline

A 2-L 4-necked flask with a water-cooled condenser, thermal probe connected to a temperature controller, heating mantle, nitrogen blanket, and overhead stirrer was charged with 80 g of 3-Cyano-7-ethoxy-4-hydroxy-6-N-acetylquinoline. The flask was charged with 1.6 L of diethylene glycol dimethyl ether or dioxane and stirred. The flask was charged with 96.0 mL of phosphorus oxychloride and warmed to 100±2° C. and maintained for 45 minutes. HPLC was used to verify that <1% (relative area) 3-Cyano-7-ethoxy-4-hydroxy-6-N-acetylquinoline remained in the reaction mixture. The mixture was cooled to 80±5° C. and 25 g celite was added. The reaction mixture was filtered and the flask and celite were washed with 3×100 mL and 1×50 mL diethylene glycol dimethyl ether.

The volume of the filtrate was reduced using a vacuum. The concentrated filtrates were added to a stirred aqueous solution of 70 g of $K_2CO_3$ in water while maintaining a temperature of <50° C. The solid was collected by filtration and washed with warm water and toluene and vacuum dried to yield 4-Chloro-3-cyano-7-ethoxy-6-N-acetylquinoline (55.7 g). Yield 65%, strength 82%, mp 250° C., $^1$H NMR (DMSO-$d_6$+CDCl$_3$) δ1.45 (t, 3H), 2.20 (s, 3H), 4.30 (q, 2H), 7.10 (m, 1H), 7.15-7.40 (m, 3H), 8.50 (s, 1H), 8.85 (s, 1H), 9.20 (s, 1H), 9.60 (s, 1H)

EXAMPLE 7

N-[-4-(3-chloro-4-fluoro-phenylamino)-3-cyano-7-ethoxy-quinoline-6-yl]-acetamide A stirred mixture of N-(4-chloro-3-cyano-7-ethoxy-6N-acetylquinoline (274.5 g, 0.947 mol), 3-chloro-4-fluoroaniline (180 g, 1.24 mol), methanesulfonic acid, (5.5 g, 0.057 mol), and 2-propanol (6.7 L) was warmed to reflux (84° C.) for 6.5 hours. After stirring overnight at room temperature, the mixture was warmed to 80° C. Water (3.2 L) containing concentrated hydrochloric acid (655 mL of 38% aqueous HCl) was added. The reaction was kept at reflux for 5 hours. The reaction mixture was cooled to 0° C.-10° C. for 1 hour. The yellow solid product is collected by vacuum filtration and washed with 20% 2-propanol/water (700 mL) and water (2×700 mL). Drying the product in vacuo at 60° C. gave 344.8 g (91%, 99% by HPLC) of 6-Amino-4-(3-chloro-4-fluoro-phenylamino)-7-ethoxy-quinoline-3-carbonitrile as a hydrochloride salt. $^1$H NMR (DMSO-$d_6$+$D_2$O) δ1.42 (t, 3H), 4.25 (q, 2H), 7.05 (m, 1H), 7.1 (s, 1H), 7.35-7.50 (m, 3H), 7.65 (dd, 1H), 8.65 (s, 1H).

EXAMPLE 8

6-Amino-4-(3-chloro-4-fluoro-phenylamino)-7-ethoxy-quinoline-3-carbonitrile

Aqueous potassium carbonate (1.0 L of 10%, 0.725 mol) was added over 30 minutes to 45 minutes to a stirred suspension of 4-(3-chloro-4-fluoroanilino)-3-cyano-7-ethoxy-6-aminoquinoline (HCl salt, 391 g, 1.00 mol), methanol (3.90 L), and water (0.90 L) maintained at 65° C. Water (1.0 L) was then added over 15 minutes. The reaction mixture is allowed to cool to room temperature and stir overnight. The reaction mixture was cooled to 0° C.-5° C. for 30 minutes. The solid product was collected by vacuum filtration. The solid was washed with water (3×100 mL, 50° C.-55° C.). Drying the product in vacuo at 60° C. gave 344.7 (97%, 99.2% by HPLC) of 6-amino-4-(3-chloro-4-fluoro-phenylamino)-7-ethoxy-quinoline-3-carbonitrile. $^1$H NMR (DMSO-$d_6$) δ1.42 (t, 3H), 4.25 (q, 2H), 5.55 (broad s, 2H), 7.05 (m, 1H), 7.2-7.3 (m, 3H), 7.38 (t, 1H), 8.4 (s, 1H), 9.22 (broad s, 1H); $^{13}$C NMR (DMSO-$d_6$) δ15.09, 64.72, 91.78, 101.46, 108.43, 117.14, 117.57, 117.85, 118.16, 120.33, 121.52, 122.72, 140.05, 145.28, 148.02, 152.31, 155.55.

For purposes of this invention an acylating agent is for example acetic anhydride, halide, and acetyl chloride.

For purposes of this invention an alkylating agent includes ethyl iodide, ethyl bromide or ethyl chloride in an inert solvent such as N,N-dimethylformamide or DMSO, N,N-dimethylacetamide, acetone, or any ketone.

For purposes of this invention a base includes alkali metal hydroxides, alkali metal acetates, pyridine, 4-dimethylaminopyridine, sodium carbonate, inorganic carbonates and potassium carbonate.

For purposes of this invention a reducing agent includes iron and ammonium chloride, sodium dithionite in an aqueous medium, and hydrogen assisted by metal catalysis with metals such as palladium and platinum dispersed on carbon or another inert support.

For purposes of this invention a solvent includes benzene, toluene, acetonitrile, diphenyl ether, or tetrahydrofuran (THF). In a preferred embodiment the solvent is a mixture of biphenyl and diphenyl ether.

For purposes of this invention a chlorine-substituting reagent includes phosphorous oxychloride and phosphorous pentachloride neat or in an inert solvent such as THF, dioxane, oxalyl chloride, thionyl chloride or 1,2-dimethoxyethane.

For purposes of this invention an acid includes hydrochloric acid, sulfuric acid, methanesulfonic acid, alkanesulfonic acids in general, p-toluenesulfonic acid, benzenesulfonic acid, mineral acids as for example hydrochloric acid, or arylsulfonic acids in general.

What is claimed is:

1. A compound consisting of N-[4-(3-chloro-4-fluoro-phenylamino)-3-cyano-7-ethoxy-quinolin-6-yl]-acetamide.

* * * * *